(12) United States Patent
Zhang

(10) Patent No.: US 10,167,264 B2
(45) Date of Patent: Jan. 1, 2019

(54) SUBSTITUTED PYRIMIDINES USEFUL AS EGFR-T790M KINASE INHIBITORS

(71) Applicant: JIANGSU MEDOLUTION LTD, Taizhou (CN)

(72) Inventor: Dawei Zhang, Thousand Oaks, CA (US)

(73) Assignee: Jiangsu Medolution Ltd, Tiazhou (CN)

( * ) Notice: Subject to any disclaimer, the term of this patent is extended or adjusted under 35 U.S.C. 154(b) by 10 days.

(21) Appl. No.: 15/115,680

(22) PCT Filed: Feb. 3, 2015

(86) PCT No.: PCT/CN2015/072179
§ 371 (c)(1),
(2) Date: Jul. 31, 2016

(87) PCT Pub. No.: WO2015/117547
PCT Pub. Date: Aug. 13, 2015

(65) Prior Publication Data
US 2017/0008856 A1    Jan. 12, 2017

Related U.S. Application Data

(60) Provisional application No. 61/965,584, filed on Feb. 4, 2014.

(51) Int. Cl.
*C07D 239/48* (2006.01)
*A61K 31/506* (2006.01)
*A61K 45/06* (2006.01)

(52) U.S. Cl.
CPC .......... *C07D 239/48* (2013.01); *A61K 31/506* (2013.01); *A61K 45/06* (2013.01)

(58) Field of Classification Search
None
See application file for complete search history.

(56) References Cited

FOREIGN PATENT DOCUMENTS

| WO | 2012061299 A1 | 5/2012 |
|----|---------------|--------|
| WO | 2013138495 A1 | 9/2013 |
| WO | 2013138502 A1 | 9/2013 |

*Primary Examiner* — Savitha M Rao
*Assistant Examiner* — Gregg Polansky
(74) *Attorney, Agent, or Firm* — Feng Tian

(57) ABSTRACT

The present invention is directed to novel pyrimidines, their derivatives, pharmaceutically acceptable salts, solvates and hydrates thereof. The compounds and compositions of the present invention have protein kinases inhibitory activities and are expected to be useful for the treatment of protein kinases and/or mutants mediated diseases and conditions.

8 Claims, No Drawings

SUBSTITUTED PYRIMIDINES USEFUL AS EGFR-T790M KINASE INHIBITORS

CROSS REFERENCE

This invention claims the benefits of U.S. Provisional Patent Application No. 61/965,584 filed on Feb. 4, 2014 which is incorporated herein by reference in its entirety.

FIELD OF THE INVENTION

The present invention is directed to inhibitors of kinase and pharmaceutically acceptable salts, solvates, hydrates, prodrugs and metabolites thereof, the preparation thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Due to their activity in numerous cellular processes, protein kinases have emerged as important therapeutic targets.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy. The human epidermal growth factor receptor (HER) tyrosine kinase family consists of four structurally related cellular receptors: the epidermal growth factor receptor (EGFR; HER1), HER2 (ErbB2), HER3 (ErbB3), and HER4.

EGFR inhibitors erlotinib and gefitinib as well as the dual EGFR/HER2 inhibitor lapatinib are FDA-approved cancer drugs that are effective against multiple solid tumor cancers. However, their effectiveness is also limited by the drug resistance that frequently emerges following treatment. Point mutations in the kinase domain of EGFR as well as upregulation of by-pass signaling pathways are frequently observed resistance mechanisms in patients treated with gefitinib and erlotinib. A single point mutation at the gate-keeper position, T790M, in EGFR kinase domain accounts for approximately 50% of acquired resistance.

Thus, the compounds that can inhibit mutant protein kinases such as EGFR-T790M activity with improved efficacy or overcome drug resistance are highly desired.

SUMMARY OF THE INVENTION

The present invention provides compounds of Formula I:

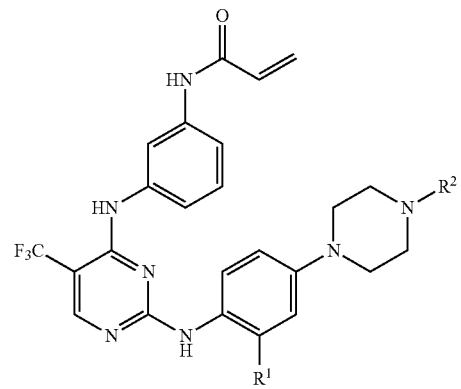

or a pharmaceutically acceptable salt, solvate or a prodrug or a stereoisomer or a tautomer or metabolite thereof, wherein $R^1$ is hydrogen, $C_1$-$C_6$ alkoxy, F, Cl, or $CF_3$;

$R^2$ is $C_1$-$C_6$ alkyl or —C(O)$R^3$;

$R^3$ is $C_1$-$C_6$ alkyl;

with the proviso that when $R^1$ is $C_1$-$C_6$ alkoxy, $R^2$ is not —C(O)$R^3$.

The present invention further provides pharmaceutical compositions comprising a compound of Formula I described above and a pharmaceutically acceptable carrier.

The present invention further provides methods for regulating the kinase signaling transduction comprising administrating to a mammalian subject a therapeutically effective amount of any of the compounds of Formula I described above.

DETAILED DESCRIPTION OF THE INVENTION

In some embodiments of the present invention, there are provided compounds of Formula I:

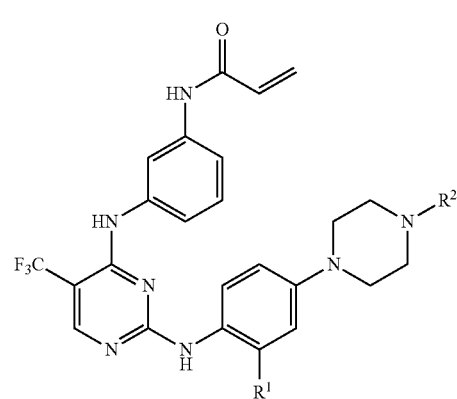

or a pharmaceutically acceptable salt, solvate or a prodrug or a stereoisomer or a tautomer or metabolite thereof, wherein $R^1$ is hydrogen, $C_1$-$C_6$ alkoxy, F, Cl, or $CF_3$;

$R^2$ is $C_1$-$C_6$ alkyl or —C(O)$R^3$;

$R^3$ is $C_1$-$C_6$ alkyl;

with the proviso that when $R^1$ is $C_1$-$C_6$ alkoxy, $R^2$ is not —C(O)$R^3$.

In certain embodiments, $R^1$ is hydrogen. In other embodiments, $R^2$ are methyl or ethyl. In other embodiments, $R^3$ is methyl. In some embodiments, $R^1$ is methoxy and $R^2$ is methyl or ethyl. In another embodiment, the deuterium enrichment in compounds of Formula I is about 1%. In other embodiments, the deuterium enrichment in the selected compounds is at least 1%.

In certain embodiments, there are provided compounds without limitation selected from the group consisting of:

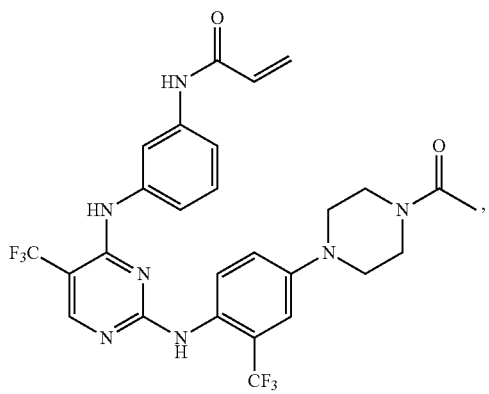

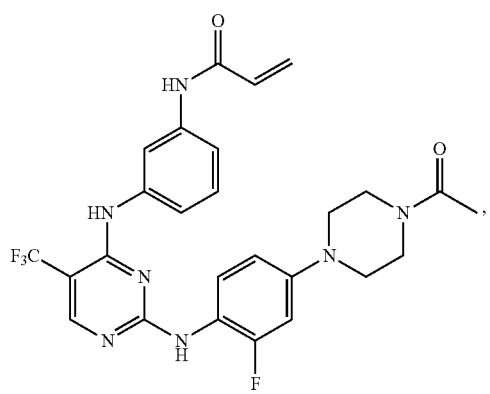

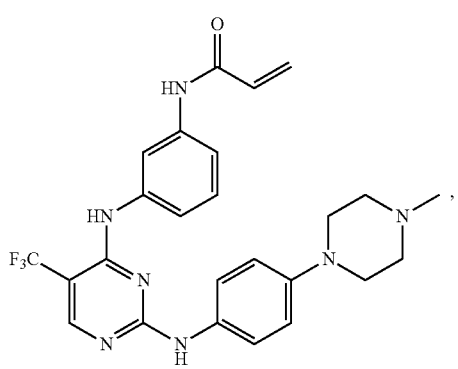

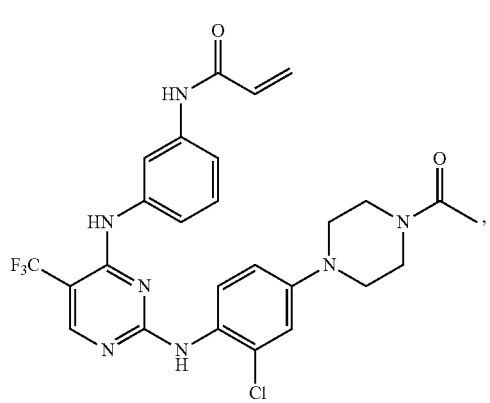

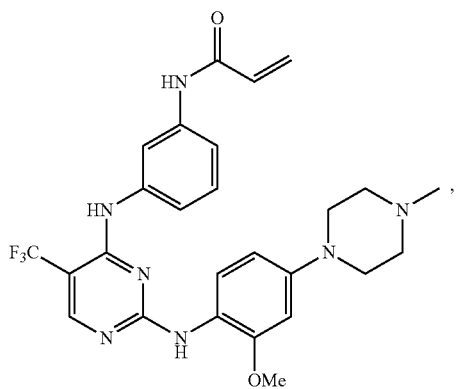

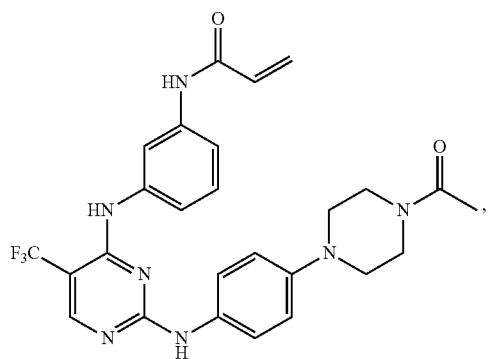

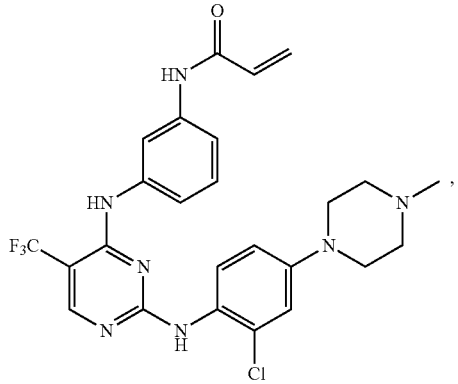

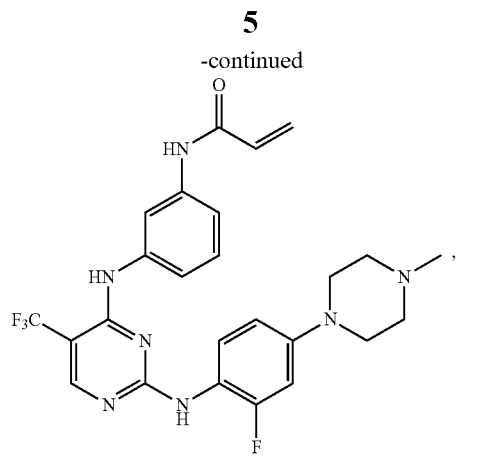
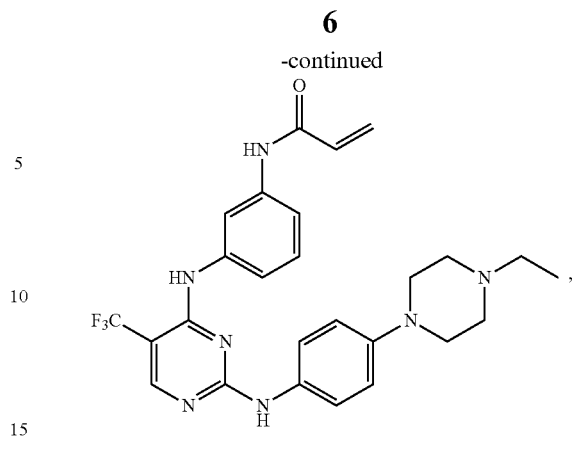
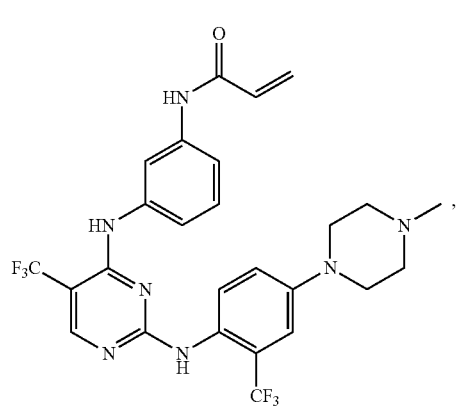
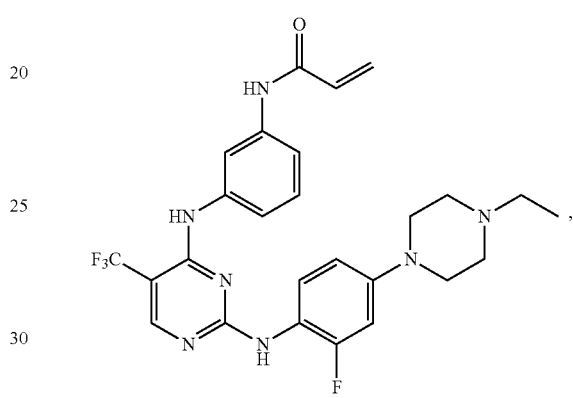
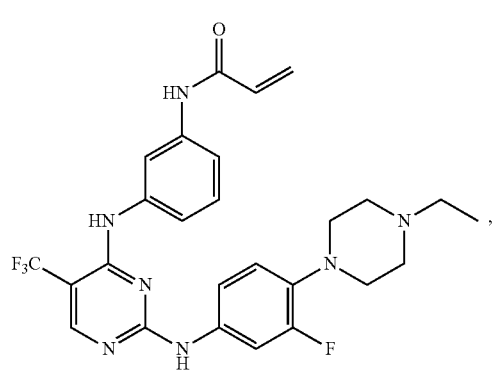
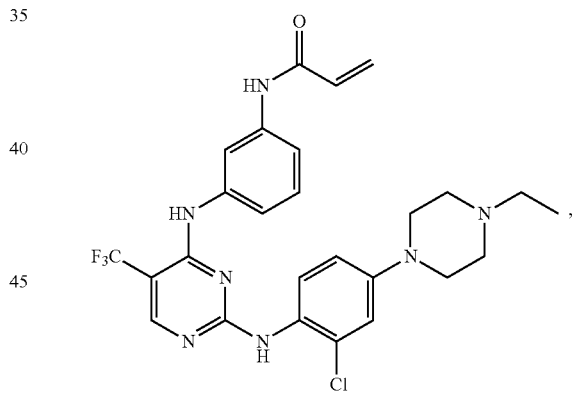
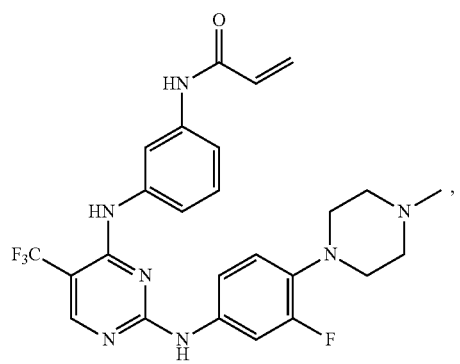
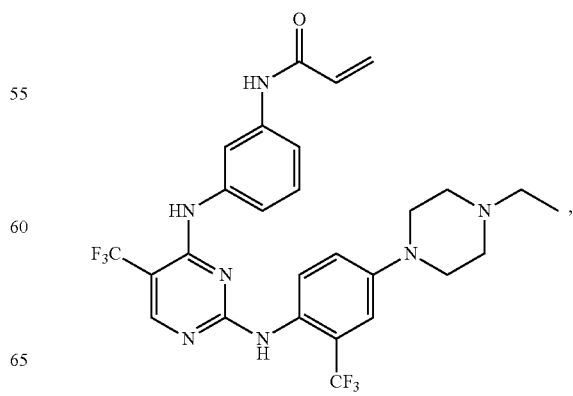

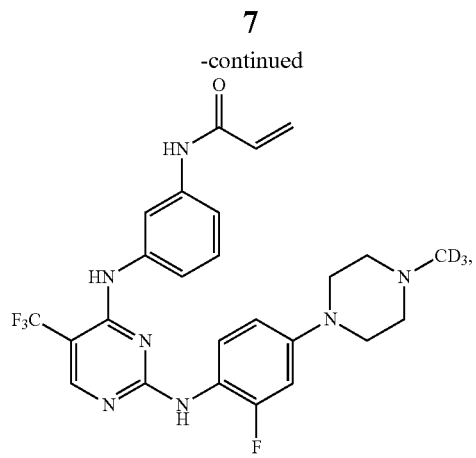
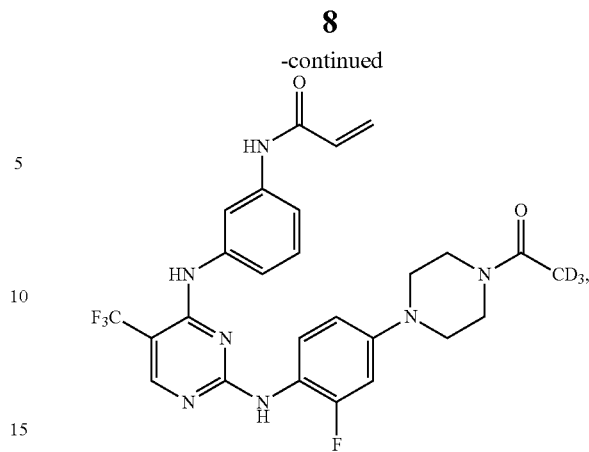
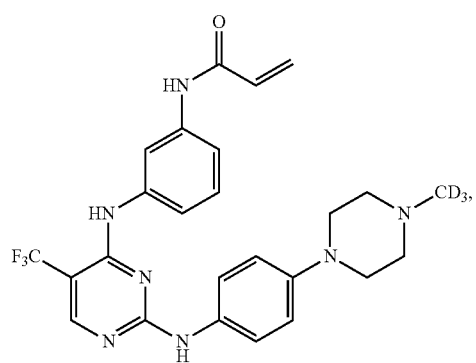
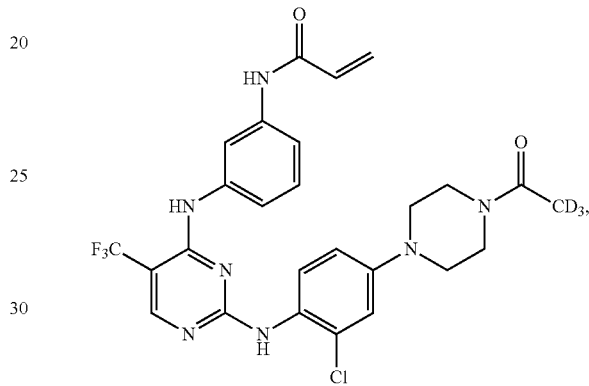
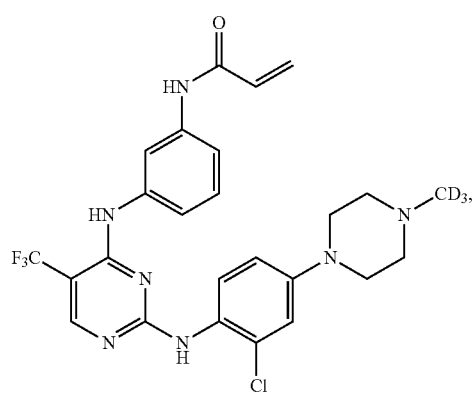
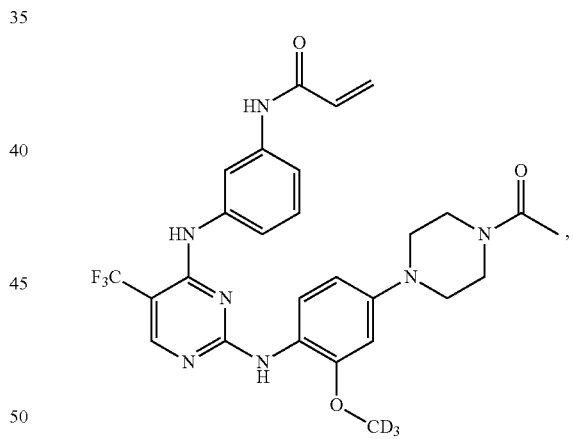
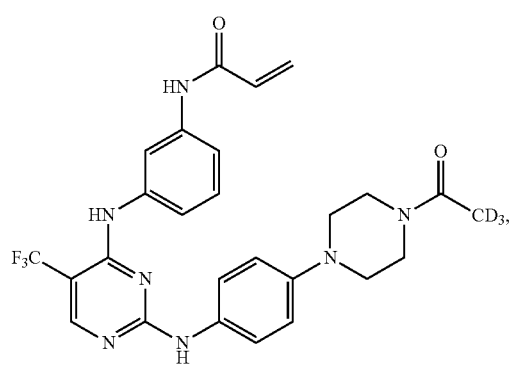
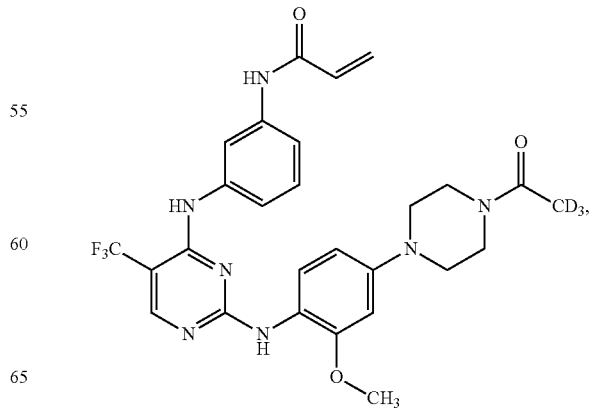

-continued

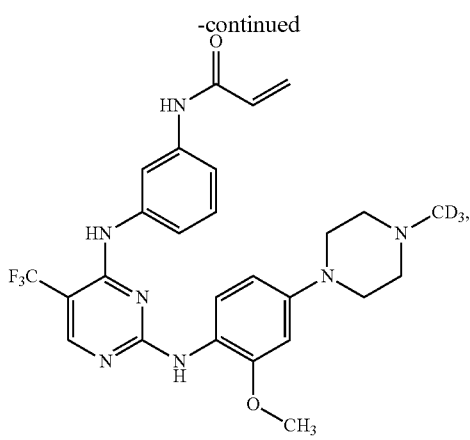

and the like, or a pharmaceutically acceptable salt, solvate, or a prodrug, or a metabolite thereof. In some embodiments, the selected compound is in the form of pharmaceutically acceptable salt. In some embodiments, the selected compound is in the form of a solvate. In other embodiments, the selected compound is in the form of a metabolite. In some embodiments, the selected compound is in the form of stereoisomer. In other embodiments, the selected compound is a tautomer. In other embodiments, the selected compound is in the form of a prodrug. In another embodiment, the deuterium enrichment in the selected compounds is about 1%. In other embodiments, the deuterium enrichment in the selected compounds is at least 1%.

In some embodiments, the present invention provides pharmaceutical compositions comprising a compound of Formula I and a pharmaceutically acceptable carrier. In certain embodiments, the compositions are for the treatment of a disease regulated by a protein kinase. In certain embodiments, the compositions are for the treatment of a hyperproliferative disorder. In other embodiments, the pharmaceutical compositions are suitable for oral, parenteral, or intravenous administration.

In some embodiments, the compound(s) of Formula I are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

In some embodiments, the present invention provides methods for regulating the kinase signaling transduction comprising administrating to a mammalian subject a therapeutically effective amount of a compound of Formula I.

In other embodiments provide herein methods for treating or preventing a HER kinases (including all mutant kinases) mediated disorder, said method comprises administrating to a mammalian subject a therapeutically effective amount of a compound of Formula I.

In yet another aspect, there are provided herein methods for inhibiting EGFR kinases, said method comprises administrating to a mammalian subject a therapeutically effective amount of a compound of Formula I.

In other embodiments provide herein methods for treating neoplasia comprising administrating to a mammalian subject in need thereof, a therapeutically effective amount of a compound of Formula I. In certain embodiments, the neoplasia is selected from liver cancer, skin cancer, leukemia, colon carcinoma, renal cell carcinoma, gastrointestinal stromal cancer, solid tumor cancer, myeloma, breast cancer, pancreatic carcinoma, non-small cell lung cancer, non-hodgkin's lymphoma, hepatocellular carcinoma, thyroid cancer, bladder cancer, colorectal cancer, and prostate cancer. In certain embodiments, the neoplasia is non-small cell lung cancer. In some embodiments, the methods further comprise administering one or more anti-cancer agents.

In other embodiments, there are provided methods for treating or preventing a hyper-proliferative comprising administrating to a mammalian subject a therapeutically effective amount of a compound of Formula I.

The following definitions should assist in understanding the invention described herein.

The term "alkyl" is intended to include straight, branched, and cyclic hydrocarbon groups, which contain only single carbon-carbon bonds and which may be unsubstituted or optionally substituted with one or more functional groups. The preferred chain length of an alkyl group is from 1 to 6 carbon atoms. $C_1$-$C_6$ alkyl is intended to include $C_1$, $C_2$, $C_3$, $C_4$, $C_5$ and $C_6$ alkyl groups. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^XR^Y$, wherein $R^X$ and $R^Y$ are independently selected from the group consisting of hydrogen, alkyl, cycloalkyl, aryl, carbonyl, acetyl, sulfonyl, trifluoromethanesulfonyl and, when $R^X$ and $R^Y$ are combined, a five- or six-member heteroalicyclic ring. Illustrative substituted alkyl groups include, but are not limited to, fluoromethyl, difluoromethyl, trifluoromethyl, aminomethyl, aminoethyl, hydoxymethyl, methoxymethyl, 2-fluoroethyl, and 2-methoxyethyl, etc.

The term "alkoxy" refers to both an —O-(alkyl) and an —O-(unsubstituted cycloalkyl) group. $C_1$-$C_6$ alkoxy is intended to include $C_1$-$C_6$ alkyl groups, wherein $C_1$-$C_6$ alkyl is defined above. Representative examples include, but are not limited to, methoxy, ethoxy, propoxy, butoxy, cyclopropyloxy, cyclobutyloxy, cyclopentyloxy, cyclohexyloxy, and the like.

Halogen means fluorine, chlorine, bromine, and iodine.

The invention also includes isotopically-labeled compounds of the invention, wherein one or more atoms are replaced by an atom having the same atomic number, but an atomic mass or mass number different from the atomic mass or mass number usually found in nature. Examples of isotopes suitable for inclusion in the compounds of the invention include isotopes of hydrogen, such as deuterium, and those of carbon, such as $^{13}C$. Certain isotopically-labeled compounds of the invention, for example, those incorporating a radioactive isotope, are useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "comprising" is meant to be open-ended, including the indicated component(s), but not excluding other elements.

The term "pharmaceutically acceptable" when used with reference to a compound of Formula I is intended to refer to a form of the compound that is safe for administration to a subject. For example, a free base, a salt form, a solvate, a hydrate, a prodrug or derivative form of a compound of Formula I, which has been approved for mammalian use, via oral ingestion or any other route of administration, by a governing authority or regulatory agency, such as the Food and Drug Administration (FDA) of the United States, is pharmaceutically acceptable.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "metabolite" as used herein means a physiologically active compound resulting from the metabolism of an inventive compound, when such compound is administered to a mammal. Metabolites of a compound may be identified using routine techniques known in the art.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I. A "pharmaceutically-acceptable prodrug" as used herein, denotes a prodrug, which is pharmaceutically acceptable.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

The protection of functional groups by protecting groups, the protecting groups themselves, and their removal reactions (commonly referred to as "deprotection") are described, for example, in standard reference works, such as J. F. W. McOmie, *Protective Groups in Organic Chemistry*, Plenum Press, London and New York (1973), in T. W. Greene, *Protective Groups in Organic Synthesis*, Wiley, New York (1981), in *The Peptides*, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the eventually desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. When synthesizing starting materials, functional groups in some cases are protected with suitable protecting groups when necessary. Protecting groups, their introduction and removal are described above.

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Indication

The present invention provides compounds which are capable of modulating one or more signal transduction pathways comprising, but not limited to, EGFR and/or all the mutants thereof, such as EGFR-T790M.

By the term "modulating," it is meant that the functional activity of the pathway (or a component thereof) is changed in the presence of a compound of Formula I in comparison to its normal activity in the absence of the compound. This effect includes changes in any quality or degree of modulation, including, increasing, agonizing, augmenting, enhancing, facilitating, stimulating, decreasing, blocking, inhibiting, reducing, diminishing, and antagonizing, etc.

The compounds of the present invention may also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effects. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), and by binding to and locking the kinase in an inactive conformation, etc.

As stated hereinbefore, the compounds defined in the present invention possess biological activities. These properties may be assessed, for example, using one or more of the procedures set out below.

Synthesis of Compounds

The compounds of Formula I were synthesized according to the procedures described in the following Schemes to those skilled in the art, wherein the substituents are as defined for Formula I above, except where further noted. The synthetic methods described below are merely exemplary, and the compounds of the invention may also be synthesized by alternate routes as appreciated by persons of ordinary skill in the art.

The synthesis of compounds of Formula I in the invention was described in the Scheme 1. The synthesis of Compound A has been reported using procedures similar to those described in the literature (WO2012061299). Compound B is commercially available or can be synthesized readily following literature procedures. The reaction of Compound A and B in solvent such as dioxane with acid such as HCl or trifluoroacetic acid generated compounds of Formula I.

Scheme 1

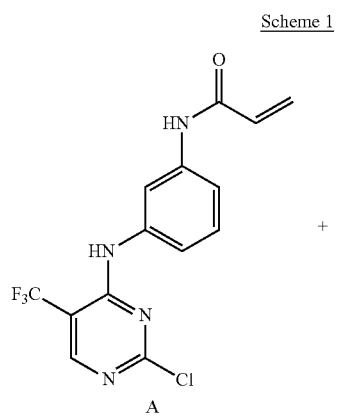

+

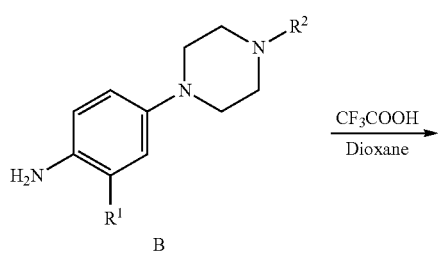

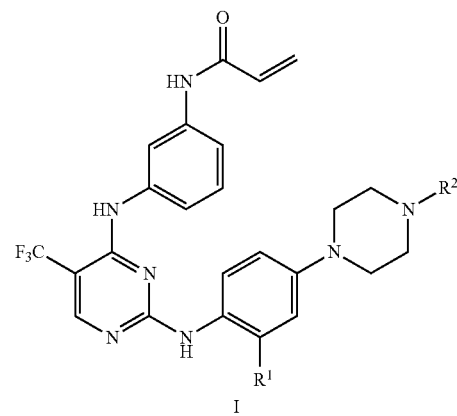

An alternative synthesis of Formula I was conducted by reaction as described in Scheme 2. The reaction of commercial available starting material compounds C and B in alcohol such as tert-butyl alcohol led to the synthesis of compound D. The replacement of chloride in compound D with compound E afforded compounds of Formula I.

Scheme 2

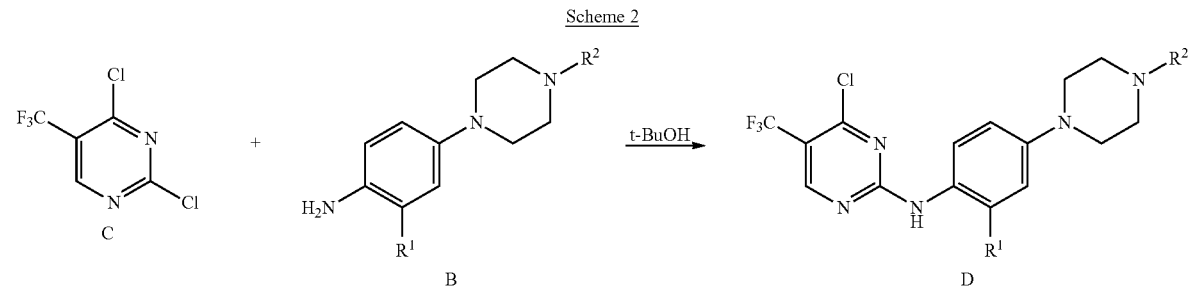

+

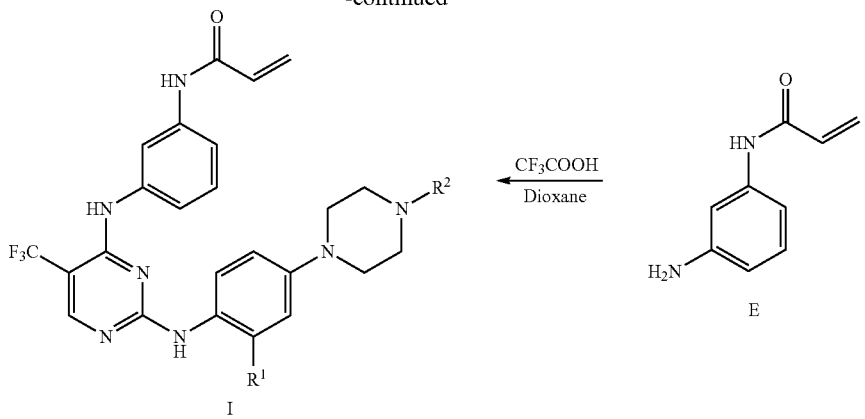

The synthesis of Compound B is described in Scheme 3. The replacement of fluoride of Compound G by Compound F afforded Compound H. The nitro group of Compound H was reduced by metal such as iron to generate Compound B.

Scheme 3

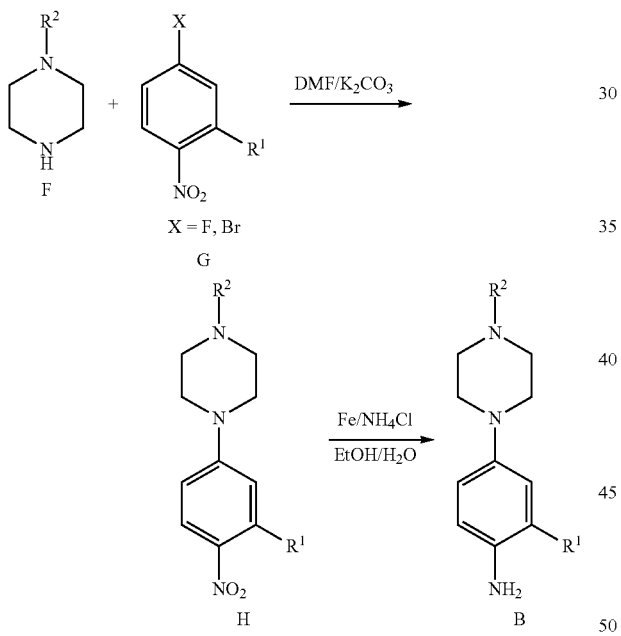

DESCRIPTION OF EMBODIMENTS

These detailed descriptions are presented for illustrative purposes only and are not intended as a restriction on the scope of the invention.

Proton NMR Spectra

Unless otherwise indicated, all $^1$H NMR spectra were run on a Varian series Mercury 300, 400 MHz instrument or a Bruker series 400 MHz instrument. Where so characterized, all observed protons are reported as parts-per-million (ppm) downfield from tetramethylsilane (TMS) or other internal reference in the appropriate solvent indicated.

Abbreviation

DMF means N,N-dimethylformamide.
DCM means dichloromethane.
DCE means dichloroethane.
DIPEA means diisopropyl ethylamine.
THF means tetrahydrofuran.
TEA means triethylamine.
TFA means trifluoroacetic acid.
EA means ethyl acetate.
RT means room temperature.

Example 1: Preparation of 4-(4-ethylpiperazin-1-yl)-2-methoxyaniline (Compound 1)

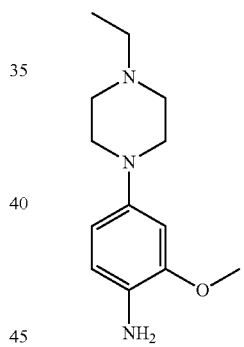

Step 1: To a solution of 1-ethylpiperazine (1.6 g, 14.0 mmol) and potassium carbonate (3.2 g, 23.4 mmol) in DMF (10 mL) was added 4-fluoro-2-methoxy-1-nitrobenzene (2.0 g, 11.7 mmol). The reaction mixture was stirred at 100° C. for 3 days, then allowed to cool to RT, diluted with H$_2$O and extracted with ether acetate. The organic phase was dried over anhydrous sodium sulfate, filtered and concentrated. The crude product 1-ethyl-4-(3-methoxy-4-nitrophenyl)piperazine was used for the next step without further purification.

Step 2: 1-Ethyl-4-(3-methoxy-4-nitrophenyl)piperazine and NH$_4$Cl (1.3 g, 23.4 mmol) were dissolved in ethanol (20 mL) and water (20 mL). The reaction mixture was heated to 50° C., then iron (2.6 g, 46.8 mmol) was added. The reaction mixture was heated to reflux for 4 hours, cooled to 50° C., filtered, and the residue was washed with ethanol. The collected filtrate was evaporated under vacuum first to remove some of the solvent (at least half thereof). The pH of the resulting solution was adjusted to 8-9 and was extracted with ethyl acetate (6×30 mL). The organic layers were combined, dried over anhydrous sodium sulfate, and concentrated. The crude product was purified by flash column chromatography on silica gel to give 4-(4-ethylpiperazin-1-yl)-2-methoxyaniline (720 mg).

Example 2: Preparation of 4-(4-ethylpiperazin-1-yl)aniline (Compound 2)

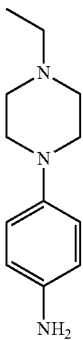

To a solution of 1-ethylpiperazine (2.1 g, 18.0 mmol, 1.2 eq) and potassium carbonate (4.2 g, 30.0 mmol, 2.0 eq) in DMF (10 mL) was added 1-bromo-4-nitrobenzene (3.0 g, 15.0 mmol, 1.0 eq). The reaction mixture was stirred at 100° C. for 3 days, allowed to cool to RT, diluted with H$_2$O and extracted with ethyl acetate. The organic phase was dried over anhydrous sodium sulfate, filtered and concentrated. The residue was purified by flash column chromatography on silica gel to give 1-ethyl-4-(4-nitrophenyl)piperazine as a yellow oil (3.2 g).

1-Ethyl-4-(4-nitrophenyl)piperazine (3.2 g, 11.9 mmol, 1.0 eq) and NH$_4$Cl (1.3 g, 23.8 mmol, 2.0 eq) was dissolved in ethanol (30 mL) and water (30 mL). The reaction mixture was heated to 50° C., then iron (2.7 g, 47.6 mmol, 4.0 eq) was added. Then the reaction mixture was heated to reflux for 3 hours, cooled to 50° C., filtered, and the residue was washed with ethanol. Most of the solvent of the collected solution was removed under vacuum, then the pH of the resulting solution was adjusted to 8-9. The resulting solution was extracted with ethyl acetate (3×100 mL). The organic layers were combined, dried over anhydrous sodium sulfate, filtered and concentrated. The crude product was purified by flash column chromatography on silica gel to give 4-(4-ethylpiperazin-1-yl)aniline (1.2 g).

Example 3: Preparation of 1-(4-(4-aminophenyl)piperazin-1-yl)ethanone (Compound 3)

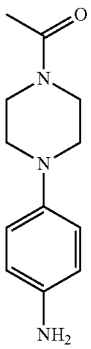

To a solution of 1-(piperazin-1-yl)ethanone (2.3 g, 18.0 mmol, 1.2 eq) and potassium carbonate (4.2 g, 30.0 mmol, 2.0 eq) in DMF (10 mL) was added 1-bromo-4-nitrobenzene (3.0 g, 15.0 mmol, 1.0 eq). The reaction mixture was stirred at 100° C. for 3 days, allowed to cool to RT, diluted with H$_2$O and extracted with ethyl acetate. The organic layers were dried over anhydrous sodium sulfate, filtered and concentrated. The resulting residue was purified by silica gel column chromatography to give 1-(4-(4-nitrophenyl)piperazin-1-yl)ethanone (1.8 g) as a yellow oil.

1-(4-(4-Nitrophenyl)piperazin-1-yl)ethanone (1.8 g, 7.2 mmol, 1.0 eq) and NH$_4$Cl (770 mg, 14.4 mmol, 2.0 eq) were dissolved in ethanol (35 mL) and water (35 mL). The reaction mixture was heated to 50° C., iron (1.6 g, 28.8 mmol, 4.0 eq) was added. Then the reaction mixture was heated to reflux for 4 hours. The reaction mixture was cooled to 50° C., filtered and washed with ethanol. Most of the solvent of the collected filtrate was removed under vacuum and the pH of the resulting solution was adjusted to 8-9, then extracted with ethyl acetate (3×100 mL). The organic layers were combined, dried over anhydrous sodium sulfate, filtered and concentrated. The crude product was purified by flash column chromatography on silica gel to give 1-(4-(4-aminophenyl)piperazin-1-yl)ethanone (1.2 g).

Example 4: Preparation of 4-(4-ethylpiperazin-1-yl)-2-fluoroaniline (Compound 4)

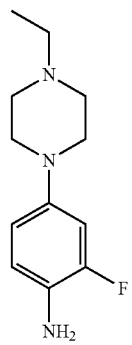 [SMILES: CCN1CCN(c2ccc(N)c(F)c2)CC1]

2,4-Difluoro-1-nitrobenzene (2.0 g, 12.6 mmol, 1.0 eq) was added to a solution of 1-ethylpiperazine (1.7 g, 15.1 mmol, 1.2 eq) and potassium carbonate (3.5 g, 25.2 mmol, 2.0 eq) in DMF (10 mL). The reaction mixture was stirred at 100° C. for 3 days, cooled to RT, diluted with H$_2$O and extracted with ethyl acetate. The organic layers were dried over anhydrous sodium sulfate, filtered and concentrated. The residue was purified by silica gel column chromatography to give the 1-ethyl-4-(3-fluoro-4-nitrophenyl)piperazine (2.9 g) as a yellow oil.

1-Ethyl-4-(3-fluoro-4-nitrophenyl)piperazine (2.9 g, 11.5 mmol, 1.0 eq) and NH$_4$Cl (1.2 g, 23.0 mmol, 2.0 eq) were dissolved in ethanol (15 mL) and water (15 mL). The reaction mixture was heated to 50° C., then iron (2.6 g, 45.8 mmol, 4.0) was added. Then the reaction mixture was heated to reflux for 3 hours. The reaction mixture was cooled to 50° C., filtered, and the residue was washed with ethanol. Most of the solvent of the collected solution was removed under vacuum and the pH of the resulting solution was adjusted to 8-9, then the resulting solution was extracted with ethyl acetate (3×100 mL). The organic layers were combined, dried over anhydrous sodium sulfate, filtered and concentrated. The crude was purified by flash column chromatography on silica gel to give 4-(4-ethylpiperazin-1-yl)-2-fluoroaniline (1.3 g).

Example 5: Preparation of 1-(4-(4-amino-3-fluorophenyl)piperazin-1-yl)ethanone (Compound 5)

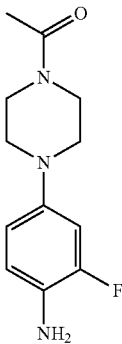

2,4-Difluoro-1-nitrobenzene (2.0 g, 12.5 mmol, 1.0 eq) was added to a mixture of 1-(piperazin-1-yl)ethanone (1.6 g, 12.5 mmol, 1.0 eq) and potassium carbonate (3.5 g, 25.0 mmol, 2.0 eq) in DMF (20 mL). The reaction mixture was stirred at 100° C. overnight, allowed to cool to RT, diluted with $H_2O$ and extracted with ethyl acetate. The organic phase was dried with anhydrous sodium sulfate, filtered and concentrated. The residue was purified by silica gel column chromatography to give 1-(4-(3-fluoro-4-nitrophenyl)piperazin-1-yl)ethanone (2.4 g) as a yellow oil.

1-(4-(3-Fluoro-4-nitrophenyl)piperazin-1-yl)ethanone (2.4 g, 8.96 mmol, 1.0 eq) and $NH_4Cl$ (961 mg, 17.9 mmol, 2.0 eq) were dissolved in ethanol (35 mL) and water (35 mL). The reaction mixture was heated to 50° C., then iron (2.0 g, 35.8 mmol, 4.0 eq) was added to the reaction mixture. Then the reaction mixture was heated to reflux for 4 hours. The reaction mixture was cooled to 50° C. and filtered through diatomaceous. The cake was washed with ethanol. Most solvent of the resulting solution was removed under vacuum. The solution was subsequently adjusted to pH 8-9 and extracted with ethyl acetate (3×100 mL). Combined organic layers were dried over anhydrous sodium sulfate, filtered and concentrated. The crude product was purified by column chromatography on silica gel to give 1-(4-(4-amino-3-fluorophenyl)piperazin-1-yl)ethanone (1.0 g).

Example 6: Preparation of 2-chloro-4-(4-ethylpiperazin-1-yl)aniline (Compound 6)

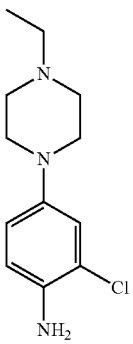

The title compound was synthesized using the similar procedure described in Example 4. Staring materials 1-(3-chloro-4-nitrophenyl)-4-ethylpiperazine and 1-ethylpiperazine were used instead.

Example 7: Preparation of 1-(4-(4-amino-3-chlorophenyl)piperazin-1-yl)ethanone (Compound 7)

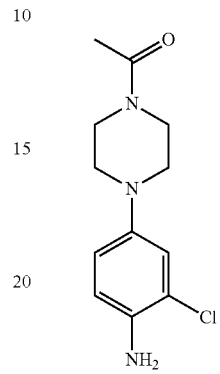

The title compound was synthesized using the similar procedure described in Example 5. Staring materials 2-chloro-4-fluoro-1-nitrobenzene and 1-(piperazin-1-yl)ethanone were used.

Example 8: Preparation of N-[3-[[2-[4-(4-acetylpiperazin-1-yl)anilino]-5-(trifluoromethyl)pyrimidin-4-yl]amino]phenyl] prop-2-enamide (Compound 8)

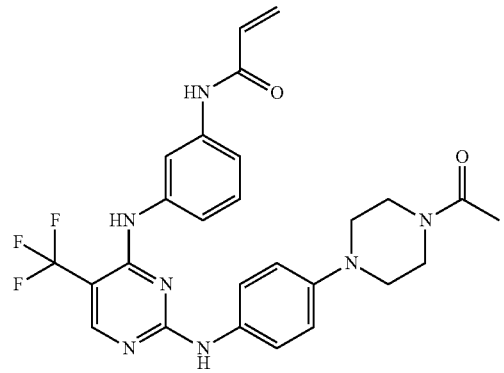 [SMILES: C=CC(=O)Nc1cccc(Nc2nc(Nc3ccc(N4CCN(C(C)=O)CC4)cc3)ncc2C(F)(F)F)c1]

To a solution of 2,4-dichloro-5-(trifluoromethyl)pyrimidine (325.5 mg, 1.5 mmol, 1.0 eq) in DCE/t-BuOH (8 mL/1 mL) at 0° C. was added $ZnCl_2$ in ether (1.0 M, 3.3 mL, 3.3 mmol, 2.2 eq). The reaction mixture was stirred at 0° C. for 1 hour and 1-(4-(4-aminophenyl)piperazin-1-yl)ethanone (400 mg, 1.84 mmol, 1.2 eq) in DCE/t-BuOH (2 mL/2 mL) was added, followed by a dropwise addition of DIPEA (213 mg, 1.65 mmol, 1.1 eq). The reaction was stirred at RT for two days and monitored by TLC. The solvent was removed under reduce pressure and the residue was dissolved in water/ethanol (26 mL, 25%) and heated to 90° C. The solution was cooled to RT over 2 hours, filtered and dried to give 1-[4-[4-[[4-chloro-5-(trifluoromethyl)pyrimidin-2-yl]amino]phenyl]piperazin-1-yl]ethanone (560 mg).

To a solution of 1-[4-[4-[[4-chloro-5-(trifluoromethyl)pyrimidin-2-yl]amino]phenyl]piperazin-1-yl]ethanone (400 mg, 1.0 mmol, 1.0 eq) and N-(3-aminophenyl)prop-2-enamide (192 mg, 1.0 mmol, 1.0 eq) in 1,4-dioxane (10 mL) was added TFA (catalytic amount) at 0° C. The reaction mixture was warmed to RT and stirred overnight. The reaction was quenched with water. The pH of the reaction mixture was adjusted to 8-9 and the mixture was extracted with ethyl acetate (3×50 mL). The organic layers were combined, dried over anhydrous sodium sulfate, filtered and concentrated. The crude product was purified by flash column chromatography on silica with EA to give crude product 240 mg. The crude product was washed with ethanol (20 mL) to give N-[3-[[2-[4-(4-acetylpiperazin-1-yl)anilino]-5-(trifluoromethyl)pyrimidin-4-yl]amino]phenyl]prop-2-enamide (160 mg). $^1$H-NMR (400 MHz, DMSO-d$_6$): δ 0.20 ppm (s, 1H), 9.51 (s, 1H), 8.73 (s, 1H), 8.32 (s, 1H), 7.74 (s, 1H), 7.63-7.65 (d, J=8.4 Hz, 1H), 7.33-7.40 (m, 3H), 7.13 (s, 1H), 6.68 (s, 1H), 6.44-6.48 (m, 1H), 6.25-6.29 (d, J=16.4 Hz, 1H), 5.76-5.78 (d, J=10.0 Hz, 1H), 3.55-3.56 (m, 4H), 2.92-2.99 (m, 4H), 2.04 (s, 3H). MS m/z 526 [M+1].

Example 9: Preparation of N-[3-[[2-[4-(4-ethylpiperazin-1-yl)anilino]-5-(trifluoromethyl)pyrimidin-4-yl]amino]phenyl]prop-2-enamide (Compound 9)

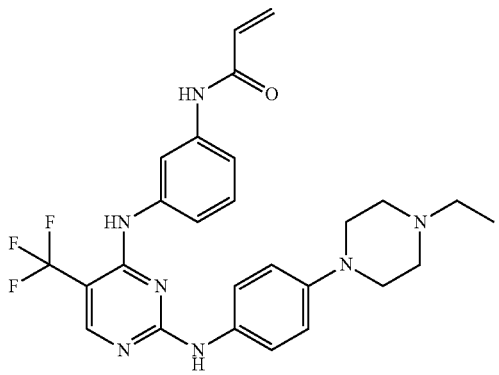 [SMILES: C=CC(=O)Nc1cccc(Nc2nc(Nc3ccc(N4CCN(CC)CC4)cc3)ncc2C(F)(F)F)c1]

To a solution of 2,4-dichloro-5-(trifluoromethyl)pyrimidine (434 mg, 2.0 mmol, 1.0 eq) in DCE/t-BuOH (8 mL/1 mL) at 0° C. was added ZnCl$_2$ in ether (4.4 mL, 4.4 mmol, 2.2 eq). The reaction mixture was stirred at 0° C. for 1 hour and 4-(4-ethylpiperazin-1-yl)aniline (410 mg, 2.0 mmol, 1.0 eq) in DCE/t-BuOH (2 mL/2 mL) was added, followed by a dropwise addition of triethylamine (222 mg, 2.2 mmol, 1.1 eq). The reaction was stirred overnight at RT and monitored by TLC. The reaction was quenched with water (30 mL), extracted with ethyl acetate (3×30 mL). The organic layers were combined, dried over anhydrous sodium sulfate, filtered and concentrated. The crude product was purified by flash column chromatography on silica gel to give 4-chloro-N-[4-(4-ethylpiperazin-1-yl)phenyl]-5-(trifluoromethyl)pyrimidin-2-amine (200 mg).

To a solution of 4-chloro-N-[4-(4-ethylpiperazin-1-yl)phenyl]-5-(trifluoromethyl)pyrimidin-2-amine (184 mg, 0.48 mmol, 1.0 eq) and N-(3-aminophenyl)prop-2-enamide (91.5 mg, 0.48 mmol, 1.0 eq) in 1,4-dioxane (10 mL) was added TFA (catalytic amount) at 0° C. The reaction mixture was warmed to RT and stirred overnight. The reaction was quenched with water and the pH of the solution was adjusted to 8-9. The resulting solution was extracted with ethyl acetate (3×30 mL). The organic layers were combined, dried over anhydrous sodium sulfate, filtered and concentrated. The crude product was purified by flash column chromatography on silica with EA to give N-[3-[[2-[4-(4-ethylpiperazin-1-yl)anilino]-5-(trifluoromethyl)pyrimidin-4-yl]amino]phenyl]prop-2-enamide (160 mg). 1H-NMR (400 MHz, DMSO-d$_6$): δ 0.02 ppm (s, 1H), 9.61 (s, 1H), 8.49 (s, 1H), 8.31 (s, 1H), 7.67 (s, 1H), 7.37-7.29 (m, 4H), 7.04-7.00 (m, 1H), 6.90 (d, J=8 Hz, 2H), 6.50-6.43 (m, 1H), 6.28-6.23 (m, 1H), 5.76 (d, J=2 Hz, 1H), 4.12-4.08 (m, 1H), 3.19-3.11 (m, 7H), 2.41-2.36 (m, 2H), 1.05 (t, J=7.2 Hz, 3H). MS m/z 512 [M+1].

Example 10: Preparation of N-[3-[[2-[4-(4-ethylpiperazin-1-yl)-2-methoxy-anilino]-5-(trifluoromethyl)pyrimidin-4-yl]amino]phenyl]prop-2-enamide (Compound 10)

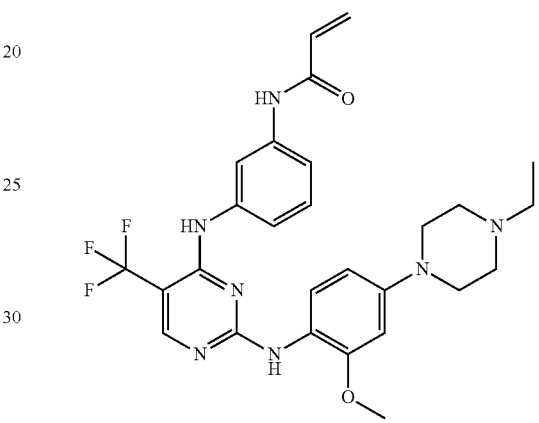

To a solution of 2,4-dichloro-5-(trifluoromethyl)pyrimidine (434 mg, 2.0 mmol, 1.0 eq) in DCE/t-BuOH (8 mL/1 mL) at 0° C. was added ZnCl$_2$ in ether (4.4 mL, 4.4 mmol, 2.2 eq). The reaction mixture was stirred at 0° C. for 1 hour and 4-(4-ethylpiperazin-1-yl)-2-methoxy-aniline (470 mg, 2.0 mmol, 1.0 eq) in DCE/t-BuOH (2 mL/2 mL) was added, followed by a dropwise addition of triethylamine (222 mg, 2.2 mmol, 1.1 eq). The reaction was stirred overnight at RT and monitored by TLC. The reaction was quenched with water (30 mL), and extracted with ethyl acetate (3×30 mL). The organic layers were combined, dried over anhydrous sodium sulfate, filtered and concentrated. The crude product was purified by flash column chromatography on silica gel to give 4-chloro-N-[4-(4-ethylpiperazin-1-yl)-2-methoxy-phenyl]-5-(trifluoromethyl)pyrimidin-2-amine (200 mg).

To a solution of 4-chloro-N-[4-(4-ethylpiperazin-1-yl)-2-methoxy-phenyl]-5-(trifluoromethyl)pyrimidin-2-amine (184 mg, 0.48 mmol, 1.0 eq) and N-(3-aminophenyl)prop-2-enamide (91.5 mg, 0.48 mmol, 1.0 eq) in 1,4-dioxane (10 mL) was added TFA (catalytic amount) at 0° C. The reaction mixture was warmed to RT and stirred overnight. The reaction was quenched with water, and the pH of the mixture was adjusted to 8-9. The resulting mixture was extracted with ethyl acetate (3×30 mL). The organic layers were combined, dried over anhydrous sodium sulfate, filtered and concentrated. The crude product was purified by flash column chromatography on silica with EA to give N-[3-[[2-[4-(4-ethylpiperazin-1-yl)-2-methoxy-anilino]-5-(trifluoromethyl)pyrimidin-4-yl]amino]phenyl]prop-2-enamide (160 mg). $^1$H-NMR (400 MHz, CDCl$_3$): δ 8.32 ppm (s, 1H), 7.99-8.02 (d, J=7.2, 1H), 7.93 (s, 1H), 7.52 (s, 1H), 7.33-7.37 (t, J=8.0, 1H), 7.22 (s, 2H), 6.88 (s, 1H), 6.55 (d, J=2.4, 1H), 6.45-6.50 (m, 2H), 6.23-6.30 (m, 1H), 5.79-5.82 (m, 1H), 3.89 (s, 3H), 3.19-3.22 (t, J=5.0, 4H), 2.64-2.66 (t, J=5.0, 4H), 2.51-2.53 (m, 2H), 2.04 (s, 3H), 1.15-1.18 (t, J=7.2, 3H). MS m/z 542 [M+1].

Example 11: Preparation of N-[3-[[2-[4-(4-acetylpiperazin-1-yl)-2-fluoro-anilino]-5-(trifluoromethyl)pyrimidin-4-yl]amino]phenyl]prop-2-enamide (Compound 11)

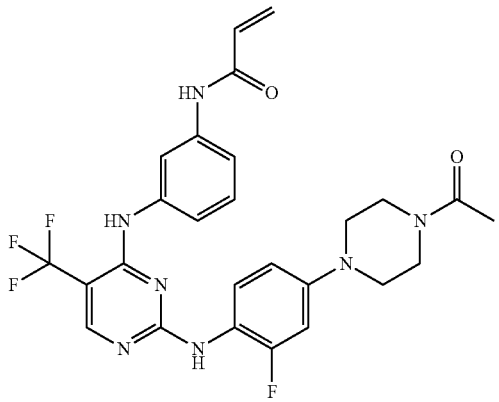

The title compound was synthesized using the similar procedure described in Example 8. Staring materials 2,4-dichloro-5-(trifluoromethyl)pyrimidine and 1-(4-(4-amino-3-fluoro-phenyl)piperazin-1-yl)ethanone were used.

Example 12: Preparation of N-[3-[[2-[4-(4-acetylpiperazin-1-yl)-2-chloro-anilino]-5-(trifluoromethyl)pyrimidin-4-yl]amino]phenyl]prop-2-enamide (Compound 12)

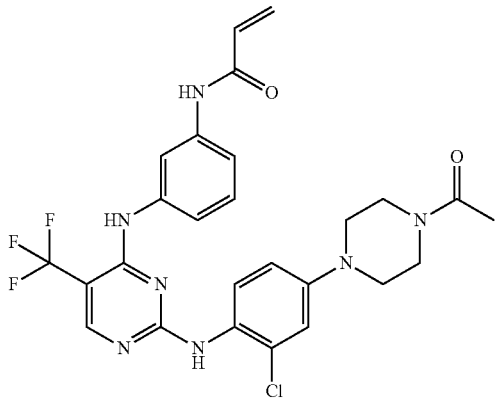 [SMILES: C=CC(=O)Nc1cccc(Nc2nc(Nc3ccc(N4CCN(C(C)=O)CC4)cc3F)ncc2C(F)(F)F)c1]

The title compound was synthesized using the similar procedure described in Example 8. Staring materials 2,4-dichloro-5-(trifluoromethyl)pyrimidine and 1-[4-(4-amino-3-chloro-phenyl)piperazin-1-yl]ethanone were used.

Example 13: Preparation of N-[3-[[2-[2-chloro-4-(4-ethylpiperazin-1-yl)anilino]-5-(trifluoromethyl)pyrimidin-4-yl]amino] phenyl]prop-2-enamide (Compound 13)

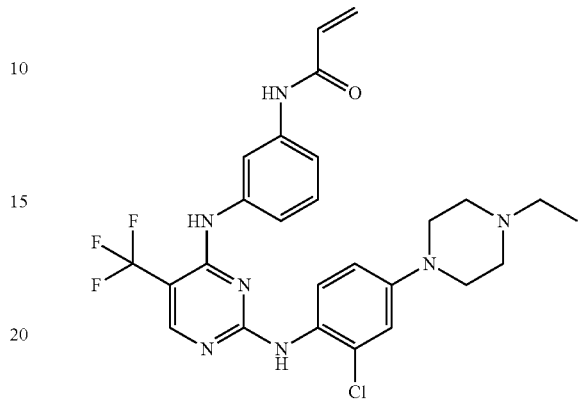

The title compound was synthesized using the similar procedure described in Example 9. Staring materials 2,4-dichloro-5-(trifluoromethyl)pyrimidine and 2-chloro-4-(4-ethylpiperazin-1-yl)aniline were used.

Example 14: Preparation of N-[3-[[2-[4-(4-ethylpiperazin-1-yl)-2-fluoro-anilino]-5-(trifluoromethyl)pyrimidin-4-yl]amino] phenyl]prop-2-enamide (Compound 14)

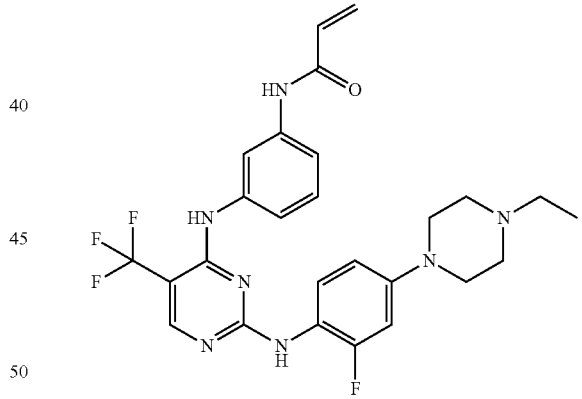

The title compound was synthesized using the similar procedure described in Example 9. Staring materials 2,4-dichloro-5-(trifluoromethyl)pyrimidine and 4-(4-ethylpiperazin-1-yl)-4-fluoro-aniline were used.

Biological Assays:

As stated herein before, the compounds defined in the present invention possess anti-proliferation activity. These properties may be assessed, for example, by using one or more of the procedures set out below:

An In Vitro Assay which Determines the Ability of a Test Compound to Inhibit EGFR (T790M/L858R) Kinase Activity:

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1× PBS, 0.05% Tween 20, 0.5 µM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Kds were determined using a compound top concentration=10,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

Binding constants (Kds) were calculated with a standard dose-response curve using the Hill equation: Response=Background+(Signal−Background)/(1+ ($Kd^{Hill\ Slope}$/$Dose^{Hill\ Slope}$)). The Hill Slope was set to −1. Curves were fitted using a non-linear least square fit with the Levenberg-Marquardt algorithm.

The following Table A lists compounds representative of the invention and their activities in EGFR (T790M/L858R) assay.

TABLE A

EGFR (T790M/L858R) Assay Results

| Compound | EGFR(T790M/L858R) Kd |
|---|---|
| CO-1686 | 1.4 nM |
| 8 | 0.54 nM |
| 9 | 0.037 nM |
| 10 | 0.28 nM |

An in vitro assay which determines the ability of a test compound to inhibit EGFR or EGFR (E746-A750del) kinase activity was performed under a similar condition to the one that has been described above for the in vitro assay which determines the ability of a test compound to inhibit EGFR (T790M/L858R) kinase activity.

The following Table B lists compounds representative of the invention and their activities in EGFR and EGFR (E746-A750del) kinases assays.

TABLE B

EGFR (E746-A750del) Assay Results

| Compound | EGFR Kd | EGFR(E746-A750del) Kd |
|---|---|---|
| WZ4002 | 46 nM | 12 nM |
| 8 | 84 nM | 26 nM |
| 9 | 15 nM | 4 nM |

A Representative Number of Compounds were Assayed Against Cancer Cell Lines NCI-H1975, Using the Cell Proliferation Assay:

1. $5 \times 10^3$ cells per well in 100 µl of medium were seeded in 96-well plate, while the medium contained 5% FBS
2. 24 hours later, 100 µl fresh medium was added with various concentrations of compounds into each well, while the medium here was free of FBS
3. After the cells were treated with compounds for 72 hours, 20 µl MTT (5 mg/ml) was added into each well, and then the assay plate was incubated at 37° C. for 4 more hours.
4. The assay plate was centrifuged at 800 g for 10 min. The medium was aspirated, 150 µl DMSO was added into each well. The plate was gently shaken for 10 min.
5. The absorbance at 570 nm was measured on the plate reader.
6. IR%=(WC−WT)/WC*100%.

The following Table C lists compounds representative of the invention and their activity in cell assays.

TABLE C

Cell Assay Results

| | CO-1686 | WZ4002 | Compound 9 | Compound 10 |
|---|---|---|---|---|
| NCI-H1975 | 910 nM | 67 nM | <10 nM | 150 nM |

In Vivo Xenograft Assay:

A representative protocol for the in vivo experiment is as follows to establish the subcutaneous NCI-H1975 cell line xenograft model in nude mice and to evaluate the in vivo therapeutic efficacy of the compounds: H1975 cells were cultured in RPMI1640 containing 10% fetal bovine serum, 1% L-glutamine, 100 U/mL penicillinG and 100 µg/mL streptomycin. Cells in logarithmic growth phase were harvested and resuspended in 1×PBS for implantation.

Tumor xenografts were established by injecting tumor cells $5 \times 10^6$/mouse into the right flank by sc under sterile conditions. When the tumors reached an appropriate size (100-200 mm$^3$), mice were randomized into 6 mice per group (8 mice in control group). The tumors were measured using a caliper in two dimensions, length (a), and width (b). Tumor volumes were estimated from measurements of two diameters of the individual tumors as follows:

$$\text{Tumor Volume (mm}^3\text{)} = (a \times b^2)/2$$

The tumor sizes and animal body weights were measured twice a week. Mice were observed daily for clinical signs. Blood samples were collected 2 hours after the last treatment, plasma samples were prepared and stored at −80° C. Tumor tissues were separated, weighed, taken picture, and subsequently stored at −80° C. for further analysis. All animal experiments were performed in accordance with the *Guidelines for Use and Care of Animals of the University of Traditional Medicine*. The parameters for in vivo efficacy evaluation were calculated according to the guidance of SFDA. Percent T/C (%) was calculated with the following formula: T/C(%)=(T$_{RTV}$/C$_{RTV}$)×100%, where T$_{RTV}$ and C$_{RTV}$ stand for relative tumor volume in treatment group and vehicle control group, respectively. Relative tumor volume (RTV) was calculated using the formula: RTV=Vt/V$_0$, where Vt represents volume on testing day, and V$_0$ represents volume on first day of treatment. Tumor growth inhibition (TGI, %) were calculated as TGI (%)=100%−T/C(%).

At the study endpoint, after blood collection, mice were practised euthanasia by cervical dislocation, the tumor tissue was collected first, then the abdominal cavity was cut open, liver and spleen were excised, and weighted after the gall-bladder was removed respectively. Organ weights between the treated versus the control groups were compared. At Day 14, Compound 8 and compound 9 showed good efficacy in the NCI-H1975 xenograft study, and compound 9 showed much better tumor growth inhibition compared with CO-1686.

The following Table D lists compounds representative of the invention and their activity in subcutaneous NCI-H1975 cell line xenograft model in nude mice described above.

TABLE D

Tumor growth inhibition (TGI, %) in NCI-H1975 xenograft model

| | Compound | | |
| --- | --- | --- | --- |
| Days | CO-1686 (30 mg/kg) | 8 (30 mg/kg) | 9 (6 mg/kg) |
| 14 | TGI = 83% | TGI = 49% | TGI = 76% |

A representative protocol for the in vivo experiment to establish the subcutaneous A431 cell line xenograft model in nude mice and to evaluate the in vivo therapeutic efficacy of the compounds is similar to the protocol described above for subcutaneous NCI-H1975 cell line xenograft model in nude mice. At Day 7, Compound 9 at 20 mg/kg (TGI=48.2%) showed better tumor growth inhibition compared with CO-1686 at 100 mg/kg (TGI=38.7%).

The following Table E lists compounds representative of the invention and their activity in subcutaneous A431 cell line xenograft model.

TABLE E

Tumor growth inhibition (TGI, %) in A431 xenograft model

| | Compound | |
| --- | --- | --- |
| Days | CO-1686 (100 mg/kg) | 9 (20 mg/kg) |
| 7 | TGI = 38.7% | TGI = 48.2% |

What is claimed is:

1. A compound according to Formula I:

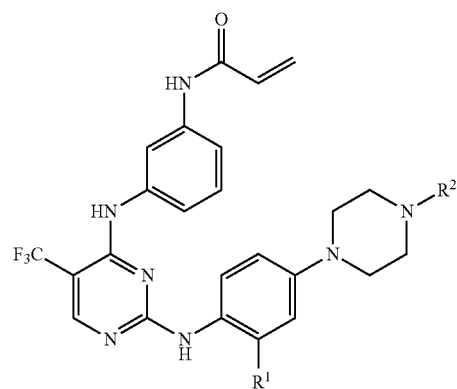

or a pharmaceutically acceptable salt, solvate, stereoisomer or tautomer thereof, wherein R$^1$ is hydrogen, C$_1$-C$_6$ alkoxy, F, Cl, or CF$_3$;

R$^2$ is C$_1$-C$_6$ alkyl or C(O)R$^3$; and

R$^3$ is C$_1$-C$_6$ alkyl;

with the proviso that when R$^1$ is C$_1$-C$_6$ alkoxy, R$^2$ is not C(O)R$^3$.

2. The compound as claimed in claim 1, wherein R' is selected from the group consisting of hydrogen and C$_1$-C$_6$ alkoxy.

3. The compound as claimed in claim 1, wherein R$^1$ is hydrogen.

4. The compound as claimed in claim 1, wherein R$^1$ is hydrogen and R$^2$ is C$_1$-C$_6$ alkyl.

5. The compound as claimed in claim 1, wherein R$^1$ is C$_1$-C$_6$ alkoxy and R$^2$ is C$_1$-C$_6$ alkyl.

6. A compound or its pharmaceutically acceptable salt, solvate, stereoisomer or tautomer thereof selected from the group consisting of:

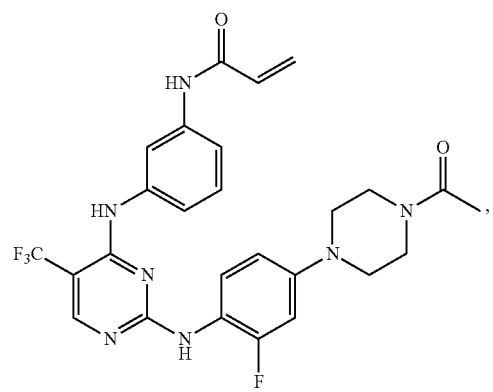

-continued
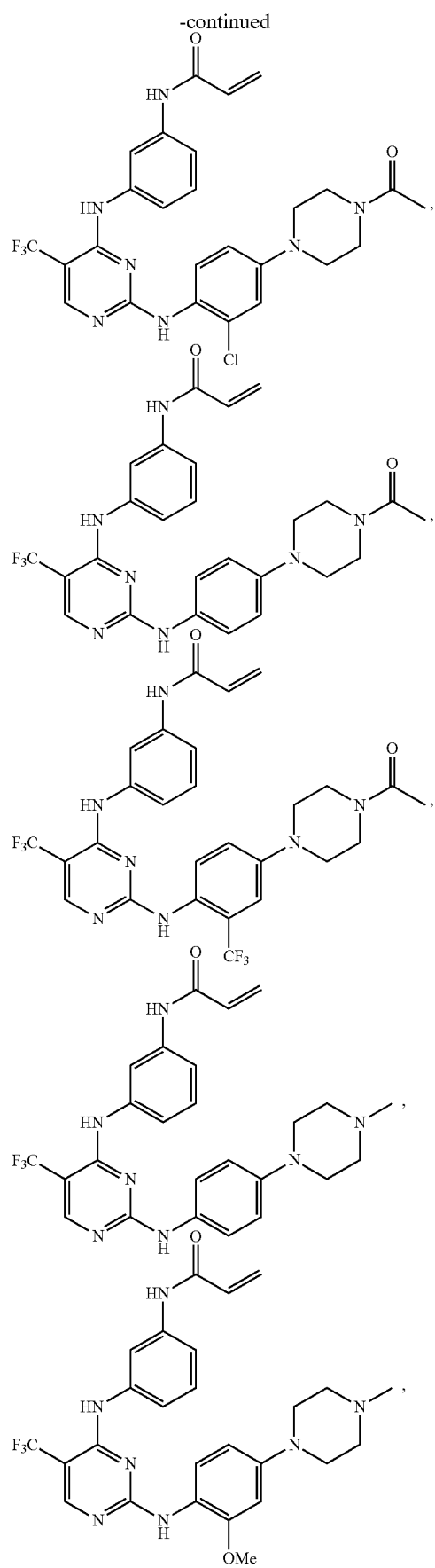
-continued
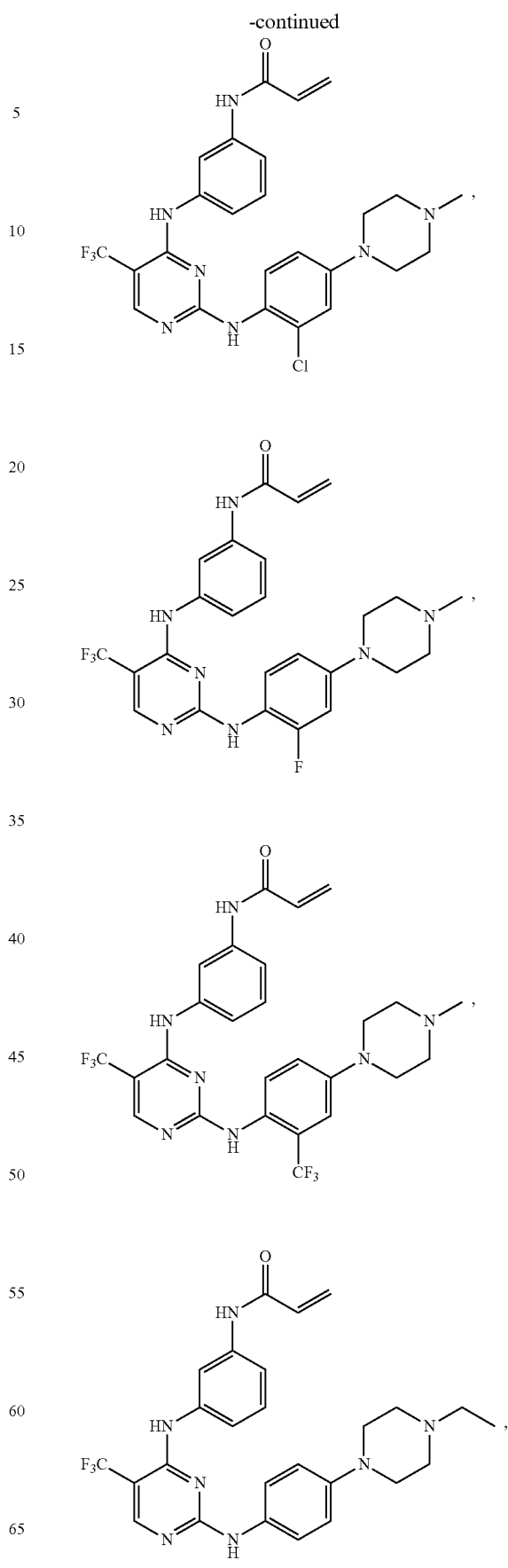

-continued
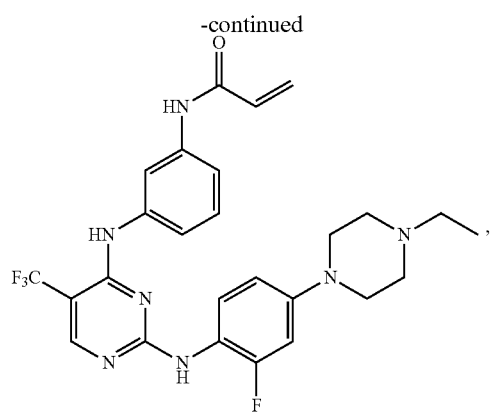
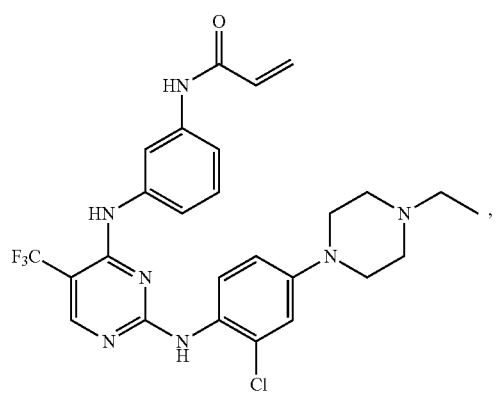
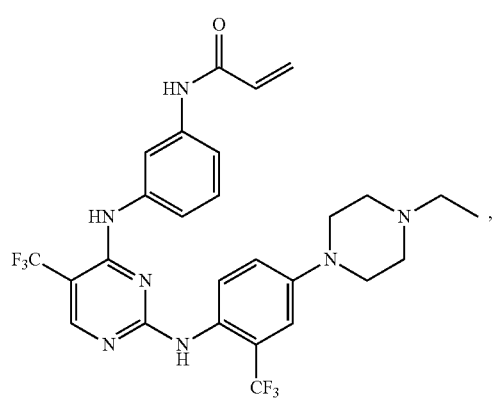
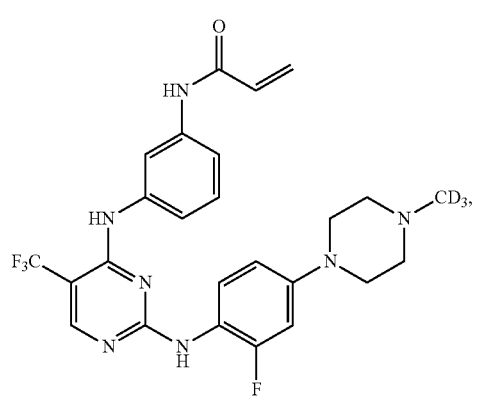
-continued
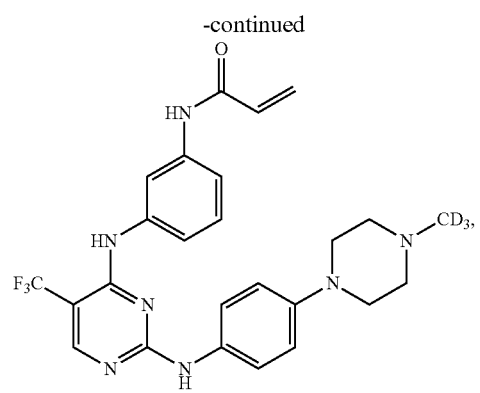
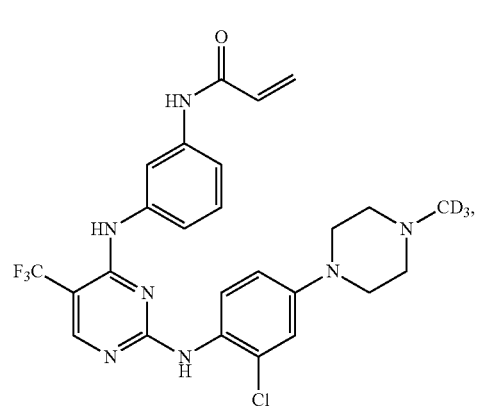
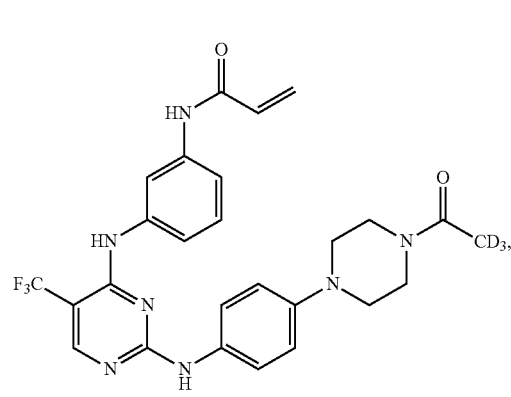
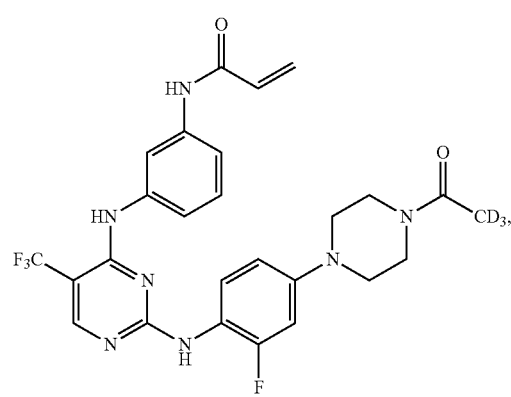

-continued

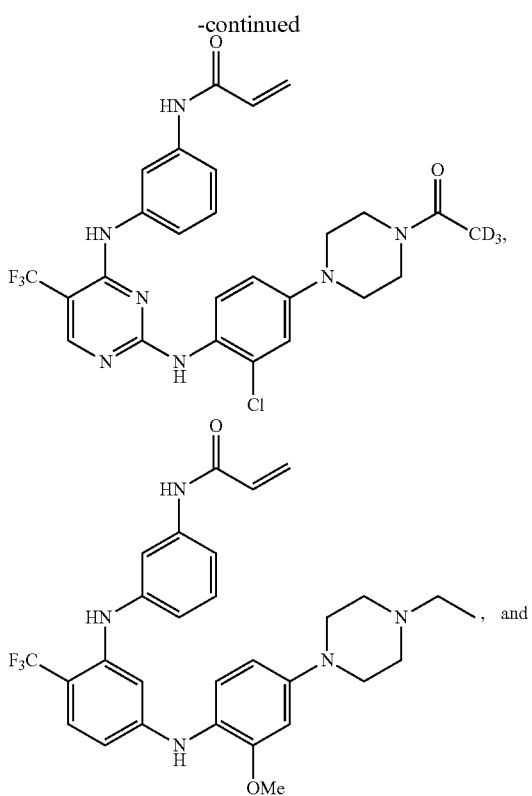

-continued

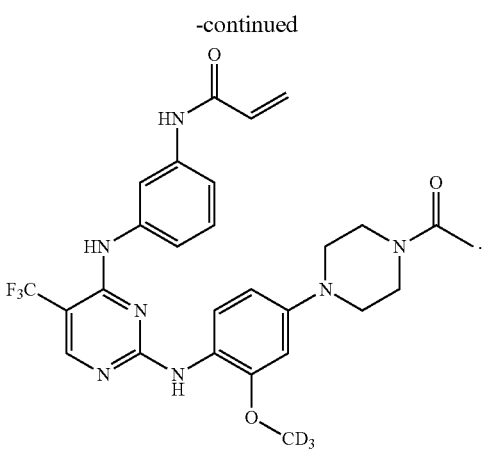

7. A pharmaceutical composition comprising a compound of claim 1 or a pharmaceutically acceptable salt thereof and a pharmaceutically acceptable carrier.

8. A method for treating neoplasia in an individual, comprising: administering to the individual a therapeutically effective amount of a pharmaceutical composition, the pharmaceutical composition comprising a compound of claim 1 or a pharmaceutical acceptable salt thereof and a pharmaceutically acceptable carrier, and wherein the neoplasia is non-small cell lung cancer.

* * * * *